United States Patent
Nuopponen

(10) Patent No.: US 10,626,191 B2
(45) Date of Patent: Apr. 21, 2020

(54) NANOFIBRILLAR CELLULOSE PRODUCT

(71) Applicant: UPM-KYMMENE CORPORATION, Helsinki (FI)

(72) Inventor: Markus Nuopponen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 15/566,824

(22) PCT Filed: May 4, 2015

(86) PCT No.: PCT/EP2015/059742
§ 371 (c)(1),
(2) Date: Oct. 16, 2017

(87) PCT Pub. No.: WO2016/177395
PCT Pub. Date: Nov. 10, 2016

(65) Prior Publication Data
US 2018/0094081 A1   Apr. 5, 2018

(51) Int. Cl.
| | |
|---|---|
| *C08B 15/02* | (2006.01) |
| *D21B 1/06* | (2006.01) |
| *C08L 1/02* | (2006.01) |
| *C12N 5/00* | (2006.01) |
| *A61K 31/717* | (2006.01) |
| *A61K 47/38* | (2006.01) |
| *A61L 2/04* | (2006.01) |
| *A61L 2/10* | (2006.01) |
| *D21B 1/02* | (2006.01) |
| *D21B 1/12* | (2006.01) |

(52) U.S. Cl.
CPC ............ *C08B 15/02* (2013.01); *A61K 31/717* (2013.01); *A61K 47/38* (2013.01); *A61L 2/04* (2013.01); *A61L 2/10* (2013.01); *C08L 1/02* (2013.01); *C12N 5/0062* (2013.01); *D21B 1/021* (2013.01); *D21B 1/06* (2013.01); *D21B 1/12* (2013.01)

(58) Field of Classification Search
CPC ............ C08B 15/02; D21B 1/021; D21B 1/06
See application file for complete search history.

(56) References Cited

U.S. PATENT DOCUMENTS

| | | | |
|---|---|---|---|
| 7,838,666 B2 | 11/2010 | Yaginuma et al. | |
| 2010/0065236 A1* | 3/2010 | Henriksson ............ | D21C 9/002 162/174 |

FOREIGN PATENT DOCUMENTS

| | | |
|---|---|---|
| WO | 2012097446 A1 | 7/2012 |
| WO | 2013117823 A1 | 8/2013 |
| WO | 2013119179 A1 | 8/2013 |
| WO | 2014049204 A1 | 4/2014 |

OTHER PUBLICATIONS

Pardo (Genome Biology 2002, 3(6): reviews 1017.1-1017.4).*
International Search Report from International Application No. PCT/EP2015/059742 dated Jul. 16, 2015.
Bhattacharya, et al., "Nanofibrillar cellulose hydrogel promotes three-dimensional liver cell culture", Journal of Controlled Release, 164, 2012, 291-298.
Pääkkö, et al., "Enzymatic Hydrolysis Combined with Mechanical Shearing and High-Pressure Homogenization for Nanoscale Cellulose Fibrils and Strong Gels", Biomacromolecules, 2007, 8, 1934-1941.

* cited by examiner

*Primary Examiner* — Pancham Bakshi
(74) *Attorney, Agent, or Firm* — Nixon Peabody LLP

(57) ABSTRACT

The present invention relates to nanofibrillar cellulose. Furthermore, the invention relates to a method for the manufacture of nanofibrillar cellulose, and to a nanofibrillar cellulose obtainable by said method. The invention also relates to uses of the nanofibrillar cellulose.

17 Claims, 5 Drawing Sheets

NANOFIBRILLAR CELLULOSE PRODUCT

CROSS-REFERENCE TO RELATED APPLICATIONS

This application is a U.S. National Stage of International Application No. PCT/EP2015/059742, filed on May 4, 2015, the contents of which are incorporated herein by reference.

FIELD OF THE INVENTION

The invention relates to nanofibrillar cellulose. Furthermore, the invention relates to a method for the manufacture of nanofibrillar cellulose, and to a nanofibrillar cellulose obtainable by said method. The invention also relates to uses of the nanofibrillar cellulose.

BACKGROUND

Nanofibrillar cellulose (NFC) has recently found applications in various areas, including biomedical and pharmaceutical applications. In higher plants, cellulose is organized in morphologically complex structure consisting of $\beta(1\rightarrow4)$ D-glucopyranose chains. These chains are laterally bound by hydrogen bonds to form microfibrils with a diameter in nanoscale, which are further organized in microfibril bundles. Furthermore, cellulose molecules are associated with other polysaccharides (hemicelluloses) and lignin in plant cell walls, resulting in even more complex morphologies. The cellulose nanoscale fibers can be released from the highly ordered structure by mechanical process, combined with other treatments such as enzymatic pretreatment.

Nanofibrillar cellulose is typically obtained by mechanical disintegration of cellulose pulp, carried out with suitable disintegration equipment. Mechanical disintegration is an energy consuming operation where the production capacity is limited. Thus several measures have been proposed for improving the grinding or fibrillation process, such as modification of pulp prior to the disintegration. Said modification may comprise chemical modification of the pulp to yield anionically or cationically charged grades of nanofibrillar cellulose (NFC). Said chemical modification may be based for example on carboxymethylation, oxidation, esterification, or etherification of cellulose molecules. However, said chemical modification methods may result in grades of NFC, which are not desirable for all applications and thus also alternative methods have been studied, such as enzymatic treatment.

U.S. Pat. No. 7,838,666 discloses a fine fibrous water-dispersible cellulose derived from a plant cell wall having starting cellulosic substance, wherein the starting cellulosic substance has an $\alpha$-cellulose content of 60-90% by weight and an average degree of polymerization of 400-1300, or the starting cellulosic substance has an $\alpha$-cellulose content of 60-100% by weight and an average degree of polymerization greater than 1300, the water-dispersible cellulose being crystalline having a crystallinity of 55% or more, and fine fibrous without entanglement between fibers, and the water-dispersible cellulose having substantially no branched bundles of fiber, the water-dispersible cellulose comprising 30% by weight or more of a component stably suspensible in water, wherein the component comprises a fibrous cellulose having a length of 0.5-30 μm and a width of 2-600 nm, and a length/width ratio of 20-400, and the water-dispersible cellulose having a loss tangent <1, when made into a 0.5% by weight aqueous dispersion.

Bhattacharya et al. 2012 disclose nanofibrillar cellulose, which contains fiber bundles with a thickness of larger than 50 nm. Although the cellulose nanofibers are very thin their organization into thick bundles results in scattering of light. Light scattering causes limitations of use of NFC hydrogel in applications requiring optical detection e.g. with light microscopy.

Pääkkö et al. 2007 disclose a method of producing cellulose fibrils using a combination of enzymatic hydrolysis and mechanical shearing. They report that previous attempts to prepare MFC only by extensive mechanical shearing resulted in that the homogenizer became blocked and the resulting material was non-homogenous. However, the enzymatic treatment leaves traces of enzymes in the end product and an additional enzyme removal or inactivation step may be required before downstream applications. Additionally, the enzymes have a significant effect on the morphology of the cellulose nanofibrils: enzymatical pre-treatment leads to decreased degree of polymerization, decreased length and decreased networking of the cellulose nanofibrils, and may lead to rod-shaped cellulose crystals or whiskers.

Accordingly, there exists a need to provide improved nanofibrillar cellulose and methods for the manufacture of nanofibrillar cellulose.

SUMMARY

The present invention is based on studies on different pretreatments of cellulose pulp prior to mechanical disintegration. It was found that mechanical disintegration into individual cellulose nanofibrils can be enhanced by a specific combination of pretreatment steps and a microfibrillar cellulose with improved properties is obtained.

An object of the invention is to provide a nanofibrillar cellulose, wherein said nanofibrillar cellulose has an average degree of polymerization greater than 1000, and wherein said nanofibrillar cellulose is of plant origin.

Another object of the invention is a method for the manufacture of nanofibrillar cellulose. The method comprises the steps of providing an aqueous suspension of cellulose pulp of plant origin, preferably of wood origin, more preferably from birch; ion-exchanging at least part of the carboxyl groups present in the cellulose pulp, preferably with $Na^+$; pre-refining said ion-exchanged cellulose pulp; subjecting said pre-refined cellulose pulp to a high pressure mechanical disintegration to obtain nanofibrillar cellulose; and optionally sterilizing said nanofibrillar cellulose; and/or optionally forming a membrane of the nanofibrillar cellulose.

The present invention also relates to a nanofibrillar cellulose obtainable by said method.

The present invention further relates to a membrane comprising the nanofibrillar cellulose as defined in the present invention or as obtained by the method of the present invention.

The present invention also relates to nanofibrillar cellulose for use as a pharmaceutical.

The present invention further relates to nanofibrillar cellulose for use in or as a matrix for drug delivery, cell delivery, tissue engineering, wound treatment, or implants, or as a wound healing agent, an anti-inflammatory agent, or a hemostatic agent.

The present invention also relates to use of nanofibrillar cellulose in or as a cosmetic, a personal care composition, a flocculant or water-treatment system, a composite, a bulking agent, a thickener, a rheology-modifier, a food additive, a paint additive, a paper, board or pulp additive, or in or as a matrix for cell or tissue culture.

The invention further relates to a pharmaceutical, cosmetic, food, agrochemical, paint, coating, paper, board, pulp, filter, composite product, adhesive, display, personal care composition, tooth paste, or cell or tissue culture matrix, or cell or tissue delivery matrix comprising the nanofibrillar cellulose of the present invention or as obtained by the method of the present invention.

DEFINITIONS

Figure 1:
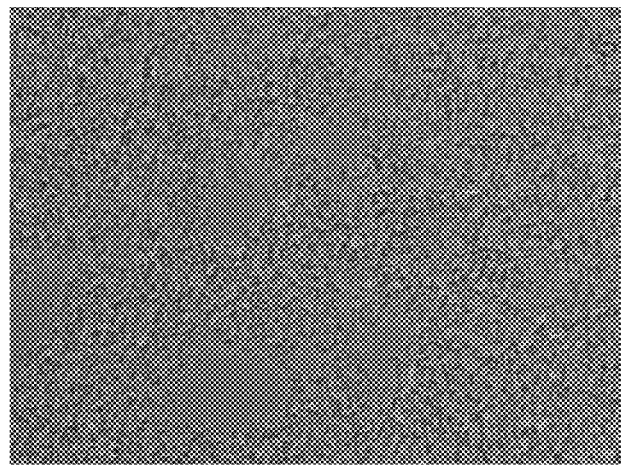
FIG. 1 presents an optical microscopy picture of the dispersion (0.8%). The width of the picture is 1200 μm.

Unless otherwise specified, the terms, which are used in the specification and claims, have the meanings commonly used in the field of pulp and paper industry, as well as in the field of cell culture. Specifically, the following terms have the meanings indicated below.

As used herein, the term "nanofibrillar cellulose" or nanofibrillated cellulose or NFC is understood to encompass nanofibrillar structures liberated from cellulose pulp. The nomenclature relating to nanofibrillar celluloses is not uniform and there is an inconsistent use of terms in the literature. For example the following terms have been used as synonyms for nanofibrillar cellulose: cellulose nanofiber, nanofibril cellulose (CNF), nanofibrillated cellulose (NFC), nano-scale fibrillated cellulose, microfibrillar cellulose, cellulose microfibrils, microfibrillated cellulose (MFC), and fibril cellulose. The smallest cellulosic entities of cellulose pulp of plant origin, such as wood, include cellulose molecules, elementary fibrils, and microfibrils. Microfibril units are bundles of elementary fibrils caused by physically conditioned coalescence as a mechanism of reducing the free energy of the surfaces. Their diameters vary depending on the source. The term "nanofibrillar cellulose" or NFC refers to a collection of cellulose nanofibrils liberated from cellulose pulp, particularly from the microfibril units. Nanofibrils have typically high aspect ratio: the length exceeds one micrometer while the diameter is typically below 100 nm. The smallest nanofibrils are similar to the so-called elementary fibrils. The dimensions of the liberated nanofibrils or nanofibril bundles are dependent on raw material, any pretreatments and disintegration method. Intact, unfibrillated microfibril units may be present in the nanofibrillar cellulose but only in insignificant amounts.

The term "cellulose pulp" refers to cellulose fibers, which are isolated from any plant based cellulose or lignocellulose raw material, using chemical, mechanical, thermo-mechanical, or chemi-thermo-mechanical pulping processes, for example kraft pulping, sulfate pulping, soda pulping, organosolv pulping. The cellulose pulp may be bleached using conventional bleaching processes.

The term "native cellulose pulp" or "native cellulose" refers here to any cellulose pulp, which has not been chemically modified after the pulping process and the optional bleaching process.

The term "suspension" refers here to a heterogeneous fluid containing solid particles and it encompasses also slurries and dispersions, typically in aqueous liquid.

The term "ion-exchanging" refers here to replacing different cations present in the cellulose pulp with a desired cation, preferably with Nat. The carboxyl groups of the cellulose, and hemicellulose if present, are transformed into their protonated form by acidifying an aqueous suspension of the cellulose pulp, followed by removing water and washing to remove the original cations and excess acid. Then a water soluble salt of the desired cation is added and the pH is adjusted to a value above 7 to replace the protons with the desired cation, followed by removing water and washing.

The term "pre-refining" refers here to a delaminating treatment of cellulose pulp. In the present invention the ion-exchanged cellulose pulp is pre-refined until a freeness of at least 60° SR (Schopper-Riegler) is achieved. The pre-refining step may comprise delamination using a PFI-mill or a refiner equipped with fibrillating blades. "Pre-refining" is not meant to encompass fibre-cutting or fibre-shortening treatments such as pre-grinding with conventional grinders, for example with Masuko grinder. Such fibre-cutting treatments deteriorate the fibers in a way which results, in combination with subsequent homogenization treatment, in products having low degree of polymerization and even resembling cellulosic fines.

The term "high pressure mechanical disintegration" refers here to disintegration of pre-refined cellulose pulp using high pressure, typically 200 bar or more, such as 1000 bar or more, resulting in liberation of cellulose nanofibrils. High pressure mechanical disintegration may be carried out for example using a pressure type homogenizer, preferably high pressure homogenizer or high pressure fluidizer, such as microfluidizer, macrofluidizer or fluidizer-type homogenizer.

The term "matrix" in connection with cells or tissues or drugs refers to a material comprising, consisting essentially of or consisting of nanofibrillar cellulose and which material is used for culturing, maintaining, transporting or delivering of cells or tissues, or for tissue engineering, or for delivering drugs, medicaments or other active agents. The nanofibrillar cellulose may be in a form or a hydrogel or membrane. Said matrix may further contain various additives such as special extra cellular matrix components, serum, growth factors, and proteins.

The term "hydrogel" in connection with nanofibrillar cellulose refers to a form where an aqueous dispersion of the nanofibrillar cellulose has a loss tangent less than 1. The term "membrane" in connection with nanofibrillar cellulose refers to a sheet-like assembly of nanofibrillar cellulose obtained by at least partial liquid removal from a dispersion of nanofibrillar cellulose.

DETAILED DESCRIPTION OF THE INVENTION

It was surprisingly found that nanofibrillar cellulose with improved properties can be obtained from cellulose pulp of plant origin using a method comprising a specific combination steps for ion-exchange, pre-refining and high pressure mechanical disintegration. The present inventors were able to obtain nanofibrillar cellulose having high degree of polymerization.

Degree of polymerization (DP) of cellulose is the number of glucose units that make up one polymer molecule. DP of cellulose nanofibrils correlates with the aspect ratio of the nanofibrils, and may thus be used for evaluating their length. The length of the nanofibrillar cellulose is related to the degree of polymerization (DP) of cellulosic chains. It can be calculated from the average intrinsic viscosity value using ISO 5351 method and parameters based on Mark-Houwink equation:

$$[\eta]=KM^a$$

parameters, a and K, are dependent on the system and in this case values K=2.28 and a=0.76 are used.

Higher DP is desirable for nanofibrillar cellulose, because it increases the inherent tensile strength of the cellulose. Strongly hydrolyzed fibers for example due to enzymatic treatment or certain chemical treatments show substantially reduced fiber length and DP, and such material is closer to microcrystalline cellulose, and the resulting microfibrils are expected to have low aspect ratio. Mechanical properties of materials based on or reinforced with nanofibrillar cellulose are dependent on fibril length. For example, DP of nanofibrillar cellulose provides information about mechanical properties of membranes prepared or reinforced using the nanofibrillar cellulose.

The obtained nanofibrillar cellulose is especially suitable for use as a matrix for cell or tissue culture, maintenance, delivery or transportation. The obtained nanofibrillar cellulose is useful also in other applications involving direct contact with cells or tissues.

Tissues are viscoelastic and are made up of cells and extracellular matrix (ECM). Matrix stiffness or strength is one of the many mechanical forces acting on cells and is appreciated as an important mediator of cell behavior. It regulates cell signaling and has an effect e.g. on growth, survival, cell alignment and motility. The optimal stiffness varies widely for different kinds of cells. For example, different types of liver cells have been reported to response in different ways to matrix stiffness. It has also been reported that human pluripotent stem cells (hPSC) form spheroids in 0.5 w % nanofibrillar cellulose hydrogel, but said spheroid formation was prevented in 1 w %.

It has also been demonstrated that the stiffness of individual collagen fibrils can be varied reproducibly and has a significant impact on cell phenotype.

Furthermore, cells are known to mechanosense over relatively short distances, roughly the width of an adjacent cell. Therefore, in a tissue, a cell is unlikely to sense mechanical forces beyond its near neighbor. Further, the cells that make up tissues are adherent, attached to some combination of their neighboring cells and surrounding ECM. Most cells require adhesion for survival.

Nanofibrillar cellulose has been reported to function well as a cell culture matrix. It is believed that the network of cellulose nanofibrils mimics extracellular matrix (ECM) supporting cell survival and proliferation. The stiffness of the nanofibrillar cellulose hydrogels can be easily adjusted by dilution. However, at the same time the consistence of the nanofibrillar cellulose hydrogels used for cell culture may have become less than optimal. This is because the previous manufacturing methods of nanofibrillar cellulose relying primarily on high pressure mechanical disintegration have provided too heterogenous material and the presence of fibril bundles among the individual nanofibrils has provided relatively stiff hydrogels even at low consistence. On the other hand manufacturing methods relying for example on enzymatic pretreatments or fiber-cutting pre-refining have provided nanofibrillar celluloses having too low DP to reach sufficient gel properties.

The present nanofibrillar cellulose has properties, which enable optimal matrix for culture of cells and tissues.

There have been difficulties in maintaining and growing cells in all the thicknesses of hydrogels. In the present invention the maintenance and growth conditions or cells are improved. The present nanofibrillar cellulose and hydrogel thereof provide optimal stiffness or strength and optimal thickness.

In the present invention the amount of required nanofibrillar cellulose may be smaller than previously for achieving the desired stiffness.

Further, higher DP is beneficial for the strength properties of a membrane when the nanofibrillar cellulose is in the form of a membrane, or when a membrane comprises the nanofibrillar cellulose of the invention as reinforcement.

A nanofibrillar cellulose of the present invention is of plant origin, preferably of wood origin, more preferably from birch. Suitably the nanofibrillar cellulose is of native cellulose pulp.

A nanofibrillar cellulose of the present invention has an average degree of polymerization greater than 1000. Preferably the average degree of polymerization (DP) of the nanofibrillar cellulose is greater than 1150 or 1200, preferably greater than 1300 or 1400, more preferably greater than 1500, 1600, 1700, or 1800.

A nanofibrillated cellulose of the present invention has a turbidity of 200 NTU or less, preferably 150 NTU or less, more preferably 130 NTU or less. The turbidity may be between 200 and 50 NTU, more preferably between 150 and 80 NTU, such as 80, 90, 100, 110, 120, 130, 140 or 150, most preferably between 130 and 100 NTU in water at concentration of 0.1 w %.

Turbidity may be measured quantitatively using optical turbidity measuring instruments. There are several commercial turbidometers available for measuring quantitatively turbidity. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

The final product has excellent gelling properties and transparency as well as homogenous structure. The transparency is due to lack of fibril bundles, which results in a homogenous structure. The transparency of the final nanofibrillar cellulose hydrogel enables optical detection of cells with light microscopy due to lower light scattering (FIG. 1).

Additionally, no autofluoresence originates from nanofibrillar cellulose. Therefore the nanofibrillar cellulose of the present invention has improved imaging properties. Use of the present nanofibrillar cellulose and hydrogel enables 3D imaging, which has not been possible previously. Furthermore, fluorescent imaging is accomplished.

The crystallinity of the present nanofibrillar cellulose may vary from 60% to 80%, preferably from 65 to 75%. The crystallinity may be for example 60%, 61%, 62%, 63%, 64%, 65%, 66%, 67%, 68%, 69%, 70%, 71%, 72%, 73%, 74%, 75%, 76%, 77%, 78%, 78%, 79%, or 80%.

A nanofibrillar cellulose preferably has a slightly anionic surface charge of −1-−5 mV. It is observed that the dispersion and dilution of nanofibrillar cellulose is made remarkably easier, if a cellulose having slightly anionic surface is used. Such surface charge is obtained when the hemicellulose content of cellulose is relatively high. Therefore, a nanofibrillar cellulose of the present invention may have hemicellulose content greater than 10 w %, preferably greater than 18 w %, more preferably greater than 20 w %. The hemicellulose content may vary between 10 and 30 w %, preferably between 18 and 28 w %; more preferably between 20 and 26 w %. The hemicellulose content may be for example 10 w %, 11 w %, 12 w %, 13 w %, 14 w %, 15 w %, 16 w %, 17 w %, 18 w %, 19 w %, 20 w %, 21 w %, 22 w %, 23 w %, 24 w %, 25 w %, 26 w %, 27 w %, 28 w %, 29 w %, or 30 w %.

It is essential that the length of fibers and aspect ratio are high enough in order to obtain satisfactory strength of the hydrogel. Typically, the DP decreases during the manufacture of nanofibrillar cellulose.

Figure 4:
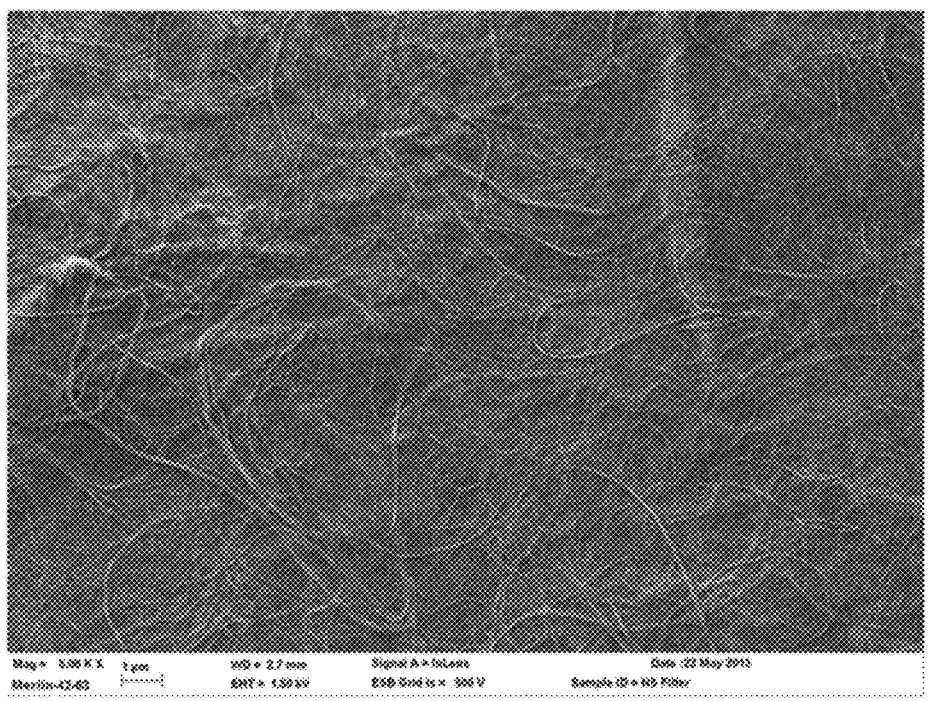
FIG. 4 presents FE-SEM image of nanofibrillar cellulose hydrogel, magnification 5 000×, scale bar 1 μm.
Figure 5:
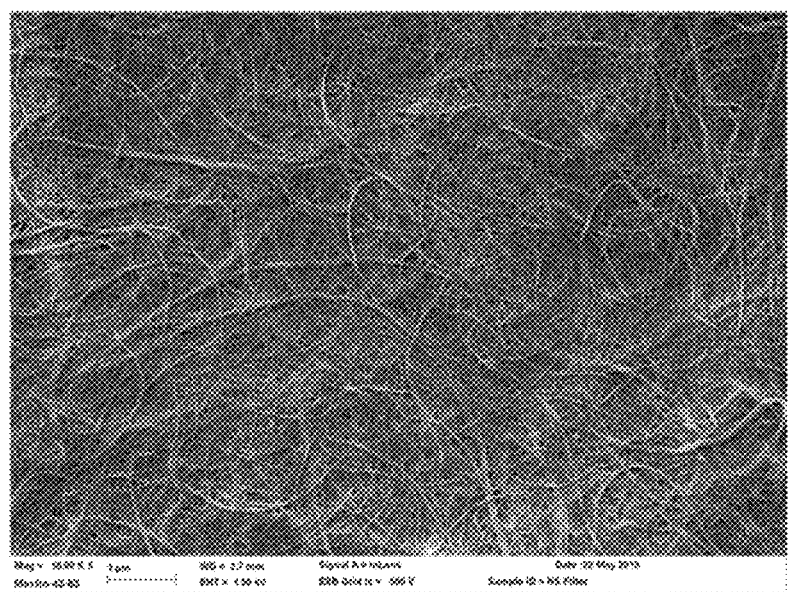
FIG. 5 presents FE-SEM image of nanofibrillar cellulose hydrogel, magnification 10 000×, scale bar 1 μm.
Figure 6:
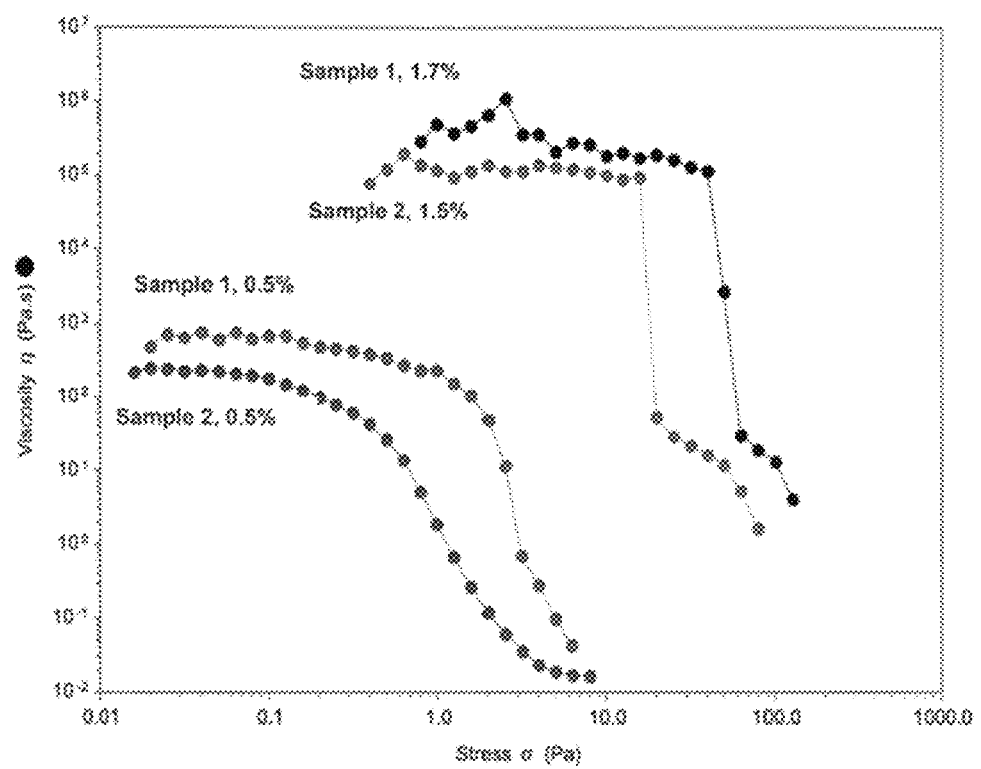
FIG. 6 presents the flow profiles of Sample 1 and Sample 2 NFC dispersions as function of applied shear stress.

In order to obtain sufficient strength of the nanocellulose hydrogel, the number-average length of the nanofibrils should be long enough, such as from 2 to 20 µm. Preferably the number-average length of the nanofibrils is between 4 and 15 µm, more preferably between 5 and 10 µm. The length of the nanofibrils may be for example 2 pm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, or 20 µm. The number average diameter is between 2 and 15 nm, preferably between 4 and 12 nm, more preferably between 6 and 10 nm. The number average diameter may be for example 2 nm, 3 nm, 4 nm, 5 nm, 6 nm, 7 nm, 8 nm, 9 nm, 10 nm, 11 nm, 12 nm, 13 nm, 14 nm, or 15 nm. An average aspect ratio is greater than 500, preferably greater than 700, more preferably greater than 900 (FIGS. 4, 5 and 6). An average aspect ratio may be for example greater than 500, 600, 700, 800 or 900.

When dispersed to a concentration of 0.5% in water, a zero shear viscosity of the present nanofibrillar cellulose may be in the range of 100-8 000 Pa·s, such as 200, 300, 400, 500, 600, 700, 800 or 900. Preferably the zero shear viscosity of the present nanofibrillar cellulose is in the range of 200-2 000 Pa·s, more preferably 300-1 000 Pa·s. A yield stress of the present nanofibrillar cellulose may be in the range of 0.5-8 Pa, preferably 1-4 Pa, when dispersed to a concentration of 0.5 w % in water. A yield stress may for example 0.5 Pa, 1 Pa, 2 Pa, 3 Pa, 4 Pa, 5 Pa, 6 Pa, 7 Pa, or 8 Pa, when dispersed to a concentration of 0.5 w % in water.

The nanofibrillar cellulose may have storage modulus between 0.3 and 20 Pa, preferably between 1 and 10, more preferably between 1 and 5, when dispersed to a concentration of 0.5 w % in water. The storage modulus may be for example 0.3 Pa, 0.4 Pa, 0.5 Pa, 0.6 Pa, 0.7 Pa, 0.8 Pa, 0.9 Pa, 1 Pa, 2 Pa, 3 Pa, 4 Pa, 5 Pa, 6 Pa, 7 Pa, 8 Pa, 9 Pa, 10 Pa, 11 Pa, 12 Pa, 13 Pa, 14 Pa, 15 Pa, 16 Pa, 17 Pa, 18 Pa, 19 Pa, or 20 Pa.

A loss tangent of the present nanofibrillar cellulose is less than 0.3, preferably less than 0.2, when dispersed to a concentration of 0.5 w % in water.

More than 90% by weight of the fibrils of the nanofibrillar cellulose, preferably more than 95% by weight, is in the fiber fraction of 0-0.2 mm.

A nanofibrillar cellulose of the present invention may be in the form of a hydrogel or a membrane.

Any cellulose pulp of any plant origin, obtained from any plant based cellulose raw material may be used as starting material. Preferably the cellulose pulp comprises secondary cell wall cellulose. Preferably plant material is of wood origin. Said wood may be selected from softwood (SW) trees, such as spruce, pine, fir, larch, douglas-fir and hemlock, from hardwood (HW) trees, such as birch, aspen, poplar, alder, eucalyptus and acacia, and from mixtures of softwoods and hardwoods. The wood may be from any hardwood belonging to family Betulaceae. Most preferably wood is from birch.

The term "cellulose pulp" refers to cellulose fibers, which are isolated from any plant based cellulose raw material, using chemical, mechanical, thermo-mechanical, or chemi-thermo-mechanical pulping processes, for example kraft pulping, sulfate pulping, soda pulping, organosolv pulping. The cellulose pulp may be bleached. Particularly cellulose pulp is of wood origin. Suitably the cellulose pulp comprises holocellulose, namely cellulose and hemicellulose. Preferably the cellulose pulp does not contain substantial amounts of lignin, or it contains only traces of lignin or non-detectable amounts of lignin. Particularly preferred cellulose pulp is bleached birch pulp.

The cellulose pulp may be native cellulose pulp. Also cellulose pulp that has been chemically modified not intended to ease the pre-refining or mechanical disintegration, but to facilitate the end-use of the nanofibrillar cellulose may be used. Such modification may be e.g. hydrophobization or labeling, or incorporation of functional side groups suitable e.g. for cell or tissue culture applications or diagnostics. Chemistry desired for the end-use may also be added to the cellulose pulp without reacting, e.g. by mixing. Preferably the nanofibrillar cellulose is of native cellulose pulp.

The cellulose pulp comprises crystalline and amorphous regions. The crystallinity of the cellulose pulp used as starting material may be at least 50%. Suitably the crystallinity of the cellulose pulp is at least 55%. Preferably the crystallinity of the cellulose pulp is at least 60%, more preferably at least 65%, most preferably at least 70%.

Enzymatic pretreatments decrease the DP because the enzymes break down the structure of the cellulose fibers and especially the amorphous regions. Chemical modifications decrease the DP depending on the used chemicals, and severity of the treatment conditions. The DP of the cellulose pulp used as a starting material in the present method for the manufacture of nanofibrillar cellulose does not decrease during the ion-exchange pretreatment.

The DP decreases during mechanical refining, especially when a cutting or fiber-shortening type of grinder is used. Here, a delamination type of pre-refining is used to avoid excessive DP decrease. The DP decreases mainly when the ion-exchanged and pre-refined cellulose pulp is subjected to a high pressure mechanical disintegration. However, the overall decrease of DP remains modest.

The cellulose pulp used as the starting material shall be selected so that the foreseen decrease in DP is taken into account. Suitably the cellulose pulp has DP greater than 2000, or greater than 2200, or greater than 2500.

Cellulose pulp of plant origin, particularly of wood origin, and where the cellulose pulp is obtained in one of the above-described methods, may be disintegrated to obtain nanofibrillar cellulose of the present invention using the procedure described hereinafter.

The method for the manufacture of nanofibrillar cellulose of the present inventions comprises the following steps 1. providing an aqueous suspension of cellulose pulp of plant origin, and ion-exchanging at least part of the carboxyl groups present in the cellulose pulp, preferably with $Na^+$;

2. pre-refining said ion-exchanged cellulose pulp;

3. subjecting said pre-refined cellulose pulp to a high pressure mechanical disintegration to obtain nanofibrillar cellulose; and optionally sterilizing said nanofibrillar cellulose; and/or optionally forming a membrane of the nanofibrillar cellulose.

1. Ion-exchange

Aqueous solution and cellulose pulp of plant origin are combined to obtain an aqueous suspension for the subsequent ion-exchange step. The solid matter content of the aqueous suspension of cellulose pulp may range from 0.1 to 20% by weight, suitably from 0.5 to 3% by weight.

The cellulose pulp of plant origin is pretreated with an ion-exchange with acid and base prior to the pre-refining and high pressure mechanical disintegration. The ion-exchange is effected by subjecting the aqueous suspension of cellulose pulp to mild acid treatment for removing positively charged ions, followed by treatment with a base containing defined, positively charged ions, for replacing the earlier ions. The pretreated cellulose pulp is subsequently pre-refined and mechanically disintegrated using high pressure.

The ion-exchange of at least part of the carboxyl groups present in the cellulose pulp, preferably with Nat, comprises adjusting the pH of the aqueous suspension of cellulose pulp to a value below 5.0, suitably below 4.0, using an inorganic or organic acid; removing of water to yield solid matter, washing the solid matter with water, and forming an aqueous suspension of the solid matter; adding at least one water soluble salt of $NH_4^+$, alkali metal or alkaline earth metal or metal to the formed suspension; adjusting the pH of the suspension to a value above 7.0 using an inorganic base; removing of water to yield solid matter, washing the solid matter with water, preferably distilled or deionized water, to yield ion-exchanged cellulose pulp; and forming an aqueous suspension of the ion-exchanged cellulose pulp.

In said ion-exchange step the water soluble salt of $NH_4^+$, alkali metal, alkaline earth metal or metal is suitably used in an amount to obtain a concentration of 0.001 to 0.01M (0.1 to 1 mol/kg fiber or solid material), particularly of 0.002 to 0.008M. In the ion-exchange the content of solid matter in the suspension may range from 0.1 to 20% by weight, suitably from 0.5 to 3% by weight.

The inorganic or organic acid is suitably an acid, which can be easily washed away, leaves no undesirable residues in the product and has a pKa-value between −7 and 7. The organic acid may be selected from short chain carboxylic acids, such as acetic acid, formic acid, butyric acid, propionic acid, oxalic acid and lactic acid. Short chain carboxylic acid refers here to C1-C8 acids. The inorganic acid may suitably be selected from hydrochloric acid, nitric acid, hydrobromic acid and sulphuric acid.

Suitably the acid is used as a dilute, from 0.001 to 5M aqueous solution, which can be conveniently added to the suspension. Suitably the addition time of the acid is between 0.2 to 24 hours. The pH is adjusted using the acid to a value below 5.0, suitably below 4.0, even more suitably below 3.0.

Water used in the method may be tap water, distilled water, deionized water, purified water or sterilized water. Suitably distilled water or deionized water is used, particularly in the washing step following the pH adjustment to more than 7.

Water removal from the suspension or slurry may be carried out by any suitable means, for example with web press, pressure filtering, suction filtering, centrifuging and screw press.

The solid matter may be washed 1-5 times, suitably 2-3 times with water after acid treatment to remove excess acid. Washing of solid matter with water may suitably be carried out after the water removal steps using the same equipment.

The water soluble salt of $NH_4^+$, alkali metal, alkaline earth metal or metal, may be selected from inorganic salts, complexes and salts formed with organic acids, of $NH_4^+$, alkali metal, alkaline earth metal or metals, suitably of $NH_4^+$, Na, K, Li, Ag and Cu. The inorganic salt is suitably sulphate, nitrate, carbonate or bicarbonate salt, such as $NaHCO_3$, $KNO_3$ or $AgNO_3$. M refers to alkali metal, alkaline earth metal or metal. According to one suitable embodiment the water soluble salt is sodium salt. The inorganic base is selected from NaOH, KOH, LiOH and $NH_3$.

The pH of the suspension is adjusted with the inorganic base to more than 7, suitably from 7.5 to 12, particularly suitably from 8 to 9. After the pH adjustment with the inorganic base, the water removal is carried out and the solid matter is washed with distilled or deionized water. Suitably the washing is repeated or carried out until the conductivity of the used washing liquid, such as filtrate, is less than 200 µS/cm, suitably less than 100 µS/cm, particularly suitably less than 20 µS/cm.

After the addition of components (acid, salt, base) to the suspensions the formed mixtures may be agitated and allowed to stand before continuing the method.

2. Pre-refining

A pre-refining step is required to prevent clogging in the subsequent mechanical disintegration step, a high pressure homogenization. It is possible to fibrillate cellulose pulp without the pre-refining step, but in that case, disintegration is troublesome and industrially un-scalable. In addition, mechanical disintegration without the pre-refining causes unnecessary shortening of the fibers. Suitable pre-refining is prerequisite to acquire hydrogel having wanted characteristics. Pre-refining is directed to the surface of fiber. Aim of the pre-refining is to fibrillate fibers externally or internally, in contrary to shortening the fibers. If cutting type treatment is used, the final degree of polymerization (DP) of the nanofibrils decrease which is unacceptable for targeted end use. The grinding type treatment (e.g. Masuko grinding) and disc and conical refiners used in pulp refining are known to shorten the fibers. It is also known that grinding causes more damage globally to the crystalline structure of cellulose decreasing the crystallinity. Compared to such equipment, the PFI mill is a very low intensity and high energy refining device. PFI produces a differing refining effect. PFI mill causes mainly internal fibrillation which is preferred pre-refining result. Also, refiners (e.g. Voith refiner) using fibrillating blades could be used to achieve suitable pre-refining result. During the pre-refining Schopper-Riegler (SR) freeness is followed for pre-refined samples. SR is widely used to track the changes in the drainage rate of various chemical pulps during beating and refining. SR value should be greater than 60 SR, such as at least 75, preferably SR is 80-85. SR measurement is done according to standard ISO 5267-1.

It is believed that by ion-exchanging at least part of the carboxyl groups that are present in the cellulose part and in the hemicellulose part of the cellulose pulp, interfibrillar repulsive forces are provided between the nanofibrils in the cellulose fibers swelling the fiber structure, and facilitating pre-refining of delamination type instead of fiber-cutting type of the ion-exchanged cellulose pulp. By this combination of pretreatments the degree of polymerization of the fibrils is not decreased as much as if the high pressure mechanical disintegration was preceded by mere mechanical refining, combination of enzymatic treatment and mechanical refining or chemical pretreatment using severe chemicals and treatment conditions.

3. Mechanical Disintegration

The obtained pre-refined cellulose pulp is subjected to a high pressure mechanical disintegration to obtain nanofibrillar cellulose. The pre-refined cellulose is subjected to the high pressure mechanical disintegration until NTU of 200 or less, preferably 150 or less, more preferably 130 NTU or less, is achieved. The turbidity may be between 200 and 50 NTU, more preferably between 150 and 80 NTU, such as 80, 90, 100, 110, 120, 130, 140 or 150, most preferably between 130 and 100 NTU in water at concentration of 0.1 w %. In this way it can be ensured that fibril bundles are substantially disintegrated and uniform nanofibrillar cellulose is obtained.

The high pressure mechanical disintegration is suitably carried out from 1 to 10 passes, particularly suitably from 1 to 5 passes. The high mechanical disintegration is carried out for example 1, 2, 3, 4, 5, 6, 7, 8, 9, or 10 passes. The pressure may range between 300-2000 bar, suitably the pressure is at least 600 bar, particularly suitably 1500 bar. The pressure may be for example 300, 400, 500, 600, 700, 800, 900, 1000, 1100, 1200, 1300, 1400, 1500, 1600, 1700, 1800, 1900, or 2000 bar.

The high pressure mechanical disintegration may be conducted using pressure type homogenizer, preferably high pressure homogenizer or high pressure fluidizer.

Optionally the obtained nanofibrillar cellulose is sterilized by autoclaving or irradiating, for example using UV irradiation.

Optionally the obtained nanofibrillar cellulose, sterilized or not, is formed into a membrane. The membrane may be formed by filtering, vacuum-filtering, pressure-filtering, casting, film coating, pan coating, electrospinning, wet spinning, dry spinning, dry-jet wet spinning, melt spinning, gel spinning, electrospraying, spraying, spray-drying, molding, pressing or extruding, or other suitable methods, optionally followed by drying. Preferably the membrane is formed from nanofibrillar cellulose with a method, comprising supplying fibril cellulose dispersion on a filter layer, draining liquid from a fibril cellulose dispersion by the effect of reduced pressure through the filter layer that is impermeable to fibrils of the fibril cellulose but permeable to the liquid to form a membrane sheet on the filter fabric, applying heat on the opposite side of the membrane sheet to the membrane sheet while continuing draining of the liquid through the filter layer by pressure difference over the filter layer, and removing the membrane sheet from the filter layer as a freestanding fibril cellulose membrane, or, alternatively keeping the filter layer in the membrane as constituent layer of a membrane product comprising the filter layer and a fibril cellulose membrane.

The membrane may be formed into a patterned membrane comprising recesses and/or protrusions.

It is possible to modify the cellulose pulp, ion-exchanged cellulose pulp, or pre-refined cellulose pulp by physical or chemical incorporation of a desired chemistry, excluding chemical modifications aiming at enhancing disintegration. Examples of a chemistry that is desired for the end-use include incorporation of functional side groups, hydrophobization, amination, labeling, addition of nutrients etc. Examples of chemical modifications aiming at enhancing the disintegration include e.g. TEMPO mediated oxidation, carboxymethylation, or cationization.

It is possible to modify the obtained nanofibrillar cellulose by incorporation of a desired chemistry, preferably by incorporation of functional side groups, hydrophobization, amination, and/or labeling. The functional side group may be for example an azide, or an amine.

Nanofibrillar cellulose is characterized by very high water retention values, a high degree of chemical accessibility and the ability to form stable gels in water or other polar solvents. Nanofibrillar cellulose product is typically a dense network of highly fibrillated celluloses. NFC may also contain some hemicelluloses; the amount is dependent on the plant source and pulping conditions.

Several different grades of NFC have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final NFC product.

NFC may be sterilized prior to use, suitably in a gel form. In addition, if desired, prior to the disintegration, the cellulose pulp may be aseptically collected from the pulp mill immediately after bleaching stage when the pulp is still sterile.

The obtained NFC has excellent gelling ability, which means that it forms a hydrogel already at a low consistency in an aqueous medium.

The nanofibrillar cellulose of the present invention is useful in cell culture applications, such as in cell culture matrix or drug delivery composition. The plant derived nanofibrillar cellulose of the present invention may be used without any modifications as biomimetic human ECM for 3D cell culture. Nanofibrilalr cellulose hydrogel is an optimal biomaterial for 3D cell scaffolds for advanced functional cell based high throughput screening assays in drug development, in drug toxicity testing and in regenerative medicine and further to drug and cell delivery in vivo. Due to its ECM-mimicking properties and non-toxicity, the nanofibrillar cellulose may be used in any kinds of applications involving cell or tissue contact, such as drug delivery, cell delivery, tissue engineering, wound treatment, or implants, or as a wound healing agent, an anti-inflammatory agent, or a hemostatic agent.

The matrix for cell culture or drug delivery composition of the present invention may further comprise suitable additives selected from the group consisting of special extra cellular matrix components, serum, growth factors, and proteins.

The present invention also relates to a cell culture or drug delivery matrix, wherein the matrix comprises living cells and the cell culture or drug delivery composition forming a hydrogel and wherein the cells are present in the matrix in a three-dimensional or two-dimensional arrangement.

Cells can be any cells. Any eukaryotic cell, such as animal cells, plant cells and fungal cells are within the scope of the present invention as well as prokaryotic cells. Prokaryotic cells comprise micro-organisms such as aerobic or anaerobic bacteria, viruses, or fungi such as yeast and molds. Even stem cells, such as non-human stem cells may be grown using the matrix comprising nanofibrillar cellulose. Depending on the cell line, the experiments are carried out on 2D or 3D, i.e. the cells are cultivated on the CNF membranes or gels or the cells are dispersed homogeneously in the CNF hydrogels or CNF membranes. Cells are growing in the 3D matrix or on the matrix. The matrix could be injectable hydrogel or sheet-like membrane optionally with appropriate surface topology. The composition comprising cellulose nanofibers or derivatives thereof can be used for immobilizing cells or enzymes.

The properties of CNF are close to optimal for cell and tissue culturing, maintenance, transporting and delivery: transparent, non-toxic, highly viscous, high suspending power, high water retention, good mechanical adhesion, non-animal based, resembles ECM dimensions, insensitive to salts, temperature or pH, not degradable, no autofluorescence. CNF has negligible fluorescence background due to the chemical structure of the material. Furthermore, CNF gel is not toxic to the cells. It is known that strong interactions are formed between adjacent nanofibrils due to the surface hydroxyl groups, and this in combination with the high stiffness results in a rigid network that improves the stiffness and strength of polymer based nanocomposites also. In addition to improved mechanical properties, the advantages with nanofibrillar cellulose as reinforcement in composites are increased thermal stability, decreased thermal expansion, and increased thermal conductivity. If a transparent composite matrix is used, it is possible to maintain most of the transparency due to the fine scale of the nanofibrils. Further, high degree of crystallinity and DP are physical properties that are useful to the elaboration of strong nanofibrillar cellulose composites.

Further, the rheological properties, transparency, non-toxicity, and insensitivity to salts, temperature or pH render the nanofibrillar cellulose desired in cosmetics, personal care compositions, flocculant or water-treatment systems, composites, as a bulking agent, a thickener, a rheology-modifier, a food additive, a paint additive, a paper, board or pulp additive. Compared to chemically modified grades, such as TEMPO oxidized grade, nanofibrillar cellulose of native cellulose is insensitive to salts, temperature or pH which may be beneficial in many end-uses.

Thereby improved pharmaceuticals, cosmetics, food, agrochemicals, paints, coatings, paper, board, pulp, filters, composite products, adhesives, displays, personal care compositions, tooth paste, or cell or tissue culture matrixes, or cell or tissue delivery matrixes may be obtained.

In aspect 1 the invention provides a nanofibrillar cellulose, wherein said nanofibrillar cellulose has an average degree of polymerization greater than 1000, and wherein said nanofibrillar cellulose is of plant origin.

Aspect 2 provides the nanofibrillar cellulose according to aspect 1, wherein said nanofibrillar cellulose has an average degree of polymerization greater than 1150, preferably greater than 1300, more preferably greater than 1500.

Aspect 3 provides the nanofibrillar cellulose according to any one of aspects 1 or 2, wherein said nanofibrillar cellulose is of wood origin, preferably from birch.

Aspect 4 provides the nanofibrillar cellulose according to any one of aspects 1 to 3, wherein said nanofibrillar cellulose is of native cellulose.

Aspect 5 provides the nanofibrillar cellulose according to any one of aspects 1 to 4, wherein said nanofibrillar cellulose has a turbidity of 200 NTU or less, preferably 150 NTU or less, more preferably 130 NTU or less, preferably the turbidity is between 200 and 50 NTU, more preferably between 150 and 80 NTU, in water at concentration of 0.1 w %.

Aspect 6 provides the nanofibrillar cellulose according to any one of aspects 1 to 5, wherein the crystallinity of the nanofibrillar cellulose is from 60% to 80%, preferably from 65% to 75%.

Aspect 7 provides the nanofibrillar cellulose according to any one of aspects 1 to 6, wherein the nanofibrillar cellulose has a hemicellulose content greater than 10 w %, preferably greater than 18 w %, more preferably greater than 20 w %.

Aspect 8 provides the nanofibrillar cellulose according to any one of aspects 1 to 7, wherein the nanofibrillar cellulose has a number average diameter between 2 and 15 nm, preferably between 4 and 12 nm, more preferably between 6 and 10 nm.

Aspect 9 provides the nanofibrillar cellulose according to any one of aspects 1 to 8, wherein the nanofibrillar cellulose has a number average length between 2 and 20 µm, preferably between 4 and 15 µm, more preferably between 5 and 10 µm.

Aspect 10 provides the nanofibrillar cellulose according to any one of aspects 1 to 9, wherein the nanofibrillar cellulose has an average aspect ratio greater than 500, preferably greater than 700, more preferably greater than 900.

Aspect 11 provides the nanofibrillar cellulose according to any one of aspects 1 to 10, wherein the nanofibrillar cellulose has a zero shear viscosity in the range of 100-8 000 Pa·s, preferably 200-2 000 Pa·s, more preferably 300-1 000 Pa·s, and a yield stress in the range of 0.5-8 Pa, preferably 1-4 Pa, when dispersed to a concentration of 0.5 w % in water.

Aspect 12 provides the nanofibrillar cellulose according to any one of aspects 1 to 11, wherein the nanofibrillar cellulose has a storage modulus between 0.3 and 20 Pa, preferably between 1 and 10, more preferably between 1 and 5, when dispersed to a concentration of 0.5 w % in water.

Aspect 13 provides the nanofibrillar cellulose according to any one of aspects 1 to 12, wherein the nanofibrillar cellulose has a loss tangent less than 0.3, preferably less than 0.2, when dispersed to a concentration of 0.5 w % in water.

Aspect 14 provides the nanofibrillar cellulose according to any one of aspects 1 to 13, wherein more than 90%, preferably more than 95% by weight of the nanofibrillar cellulose is in the fiber fraction of 0-0.2 mm.

Aspect 15 provides the nanofibrillar cellulose according to any one of aspects 1 to 14, wherein the nanofibrillar cellulose is in the form of a hydrogel or a membrane.

Aspect 16 provides a method for the manufacture of nanofibrillar cellulose, wherein the method comprises the steps of providing an aqueous suspension of cellulose pulp of plant origin, preferably of wood origin, more preferably from birch; ion-exchanging at least part of the carboxyl groups present in the cellulose pulp, preferably with $Na^+$; pre-refining said ion-exchanged cellulose pulp; subjecting said pre-refined cellulose pulp to a high pressure mechanical disintegration to obtain nanofibrillar cellulose; and optionally sterilizing said nanofibrillar cellulose, preferably by autoclaving or irradiating; and/or optionally forming a membrane of the nanofibrillar cellulose.

Aspect 17 provides the method according to aspect 16, wherein the method further comprises modifying said cellulose pulp, said ion-exchanged cellulose pulp, or said pre-refined cellulose pulp by physical or chemical incorporation of a desired chemistry, excluding chemical modifications aiming at enhancing disintegration, and/or wherein the method comprises modifying said nanofibrillar cellulose by incorporation of a desired chemistry, preferably functional side groups, hydrophobization, amination, and/or labeling.

Aspect 18 provides the method according to any one of aspects 16 or 17, wherein the ion-exchanging comprises adjusting the pH of the aqueous suspension of cellulose pulp to a value below 5.0 using an inorganic or organic acid; removing of water to yield solid matter, washing the solid matter with water, and forming an aqueous suspension of the solid matter; adding at least one water soluble salt of $NH_4^+$, alkali metal or alkaline earth metal or metal to the formed suspension; adjusting the pH of the suspension to a value above 7.0 using an inorganic base; removing of water to yield solid matter, washing the solid matter with water, preferably distilled or deionized water, to yield ion-exchanged cellulose pulp; and forming an aqueous suspension of the ion-exchanged cellulose pulp.

Aspect 19 provides the method according to any one of aspects 16 to 18, wherein the ion-exchanged cellulose pulp is pre-refined until a freeness of at least 75° SR (Schopper-Riegler), preferably of at least 80° SR, is achieved.

Aspect 20 provides the method according to any one of aspects 16 to 19, wherein the pre-refining comprises subjecting the ion-exchanged cellulose pulp to a delamination using a PFI-mill or a refiner equipped with fibrillating blades.

Aspect 21 provides the method according to any one of aspects 16 to 20, wherein the pre-refined cellulose is subjected to the high pressure mechanical disintegration until NTU of 200 or less, preferably 150 or less, is achieved.

Aspect 22 provides the method according to any one of aspects 16 or 21, wherein the high pressure mechanical disintegration is conducted using pressure type homogenizer, preferably high pressure homogenizer or high pressure fluidizer.

Aspect 23 provides the method according to any one of aspects 16 to 22, wherein the membrane is formed by filtering, vacuum-filtering, pressure-filtering, casting, film coating, pan coating, electrospinning, wet spinning, dry spinning, dry-jet wet spinning, melt spinning, gel spinning, electrospraying, spraying, spray-drying, molding, pressing or extruding, or other suitable methods, optionally followed by drying.

Aspect 24 provides a nanofibrillar cellulose obtainable by the method of any one of aspects 16 to 23.

Aspect 25 provides a membrane comprising the nanofibrillar cellulose as defined in any one of aspects 1 to 15 or 24 or as obtained by the method of any one of aspects 16 to 23.

Aspect 26 provides nanofibrillar cellulose according to any one of aspects 1 to 15 or 24 or as obtained by the method of any one of aspects 16 to 23 for use as a pharmaceutical.

Aspect 27 provides nanofibrillar cellulose according to any one of aspects 1 to 15 or 24, or as obtained by the method of any one of aspects 16 to 23 for use in or as a matrix for drug delivery, cell delivery, tissue engineering, wound treatment, or implants, or as a wound healing agent, an anti-inflammatory agent, or a hemostatic agent.

Aspect 28 provides use of nanofibrillar cellulose according to any one of aspects 1 to 15 or 24 or as obtained by the method of any one of aspects 16 to 23 in a cosmetic, a personal care composition, a flocculant or water-treatment system, a composite, a bulking agent, a thickener, a rheology-modifier, a food additive, a paint additive, a paper, board or pulp additive, or in or as a matrix for cell or tissue culture.

Aspect 29 provides a pharmaceutical, cosmetic, food, agrochemical, paint, coating, paper, board, pulp, filter, composite product, adhesive, display, personal care composition, tooth paste, or cell or tissue culture matrix, or cell or tissue delivery matrix comprising the nanofibrillar cellulose as defined in any one of aspects 1 to 15 or 24 or as obtained by the method of any one of aspects 16 to 23.

The following examples are illustrative embodiments of the present invention as described above, and they are not meant to limit the invention in any way.

EXAMPLES

Materials

Birch kraft pulp, which was used as a starting cellulose substance, has a following cellulose contents: α-cellulose 78%, β-cellulose 9%, γ-cellulose 11% (method: Alpha-, beta, and gamma-cellulose in pulp, reaffirmation of Tappi 203 cm-99).

Methods

The measurements mentioned in the examples were carried out in the following manner.

Schopper-Riegler (SR) measurement was done according to standard ISO 5267-1.

Turbidity

A nanofibrillar cellulose sample was diluted in water to a concentration below the gel point of said nanofibrillar cellulose, and turbidity of the diluted sample was measured. The turbidity of the nanofibrillar cellulose samples was measured at the concentration of 0.1%. HACH P2100 Turbidometer with a 50 ml measuring vessel was used for turbidity measurements. The dry matter of the nanofibrillar cellulose sample was determined and 0.5 g of the sample, calculated as dry matter, was loaded in the measuring vessel, which was filled with tap water to 500 g and vigorously mixed by shaking for about 30 s. Without delay the aqueous mixture was divided into 5 measuring vessels, which were inserted in the turbidometer. Three measurements on each vessel were carried out. The mean value and standard deviation were calculated from the obtained results, and the final result was given as NTU units. The novel nanofibrillar cellulose product had a typical turbidity below 200, preferably below 150 NTU in the above mentioned measurement conditions.

Degree of Polymerization (DP)

The length of the nanofibrillar cellulose is related to the degree of polymerization (DP) of cellulosic chains. Cellulose samples were dissolved in a cupriethylenediamine (CED) solution. From the solutions (starting material and the final product) a viscosity was measured and limiting viscosity number was calculated. DP was calculated from the average intrinsic viscosity value using ISO 5351 method and parameters based on Mark-Houwink equation:

$$[\eta]=KM^a$$

parameters, a and K, are dependent on the system and in this case values K=2.28 and a=0.76 were used.

Fiber Size Distribution

Fiber size distribution of the gels was determined using Metso FS5 fiber analyzer. 1 g of fibrillated cellulose was diluted in two steps to obtain a trial sample: 1.60 mg fibers in 50 ml water. Sample was fed to fiber analyzer. Sample fiber size is clearly decreased by the treatment.

Crystallinity

X-ray diffraction (XRD) analysis was done to define crystallinity index of the samples. The samples were pressed into tablets prior the analysis. The diffractograms were recorded with a Philips X'Pert MPD X-ray diffractometer in the powder method in a range 5-40° 2θ. Graphite-monochromatized Cu Kα radiation (λ=0.1541 nm). The working conditions were 40 kV and 50 mA tube power. The crystallinity indexes were calculated using the Segal method.

The Field Emission Scanning Electron Microscopy

The field emission scanning electron microscopy (FE-SEM, Sigma VP, Zeiss GmbH) pictures were taken from the dispersion at 0.1 wt % concentration. In lens SE detector was used when imaging in the secondary electron mode. Low acceleration voltages between 1.5 to 2.5 keV were used. Width and length of the nanofibrillar cellulose fibrils were measured from the pictures.

Rheological Measurements

To verify the success of fibrillation, rheological measurements of the samples in the form of nanofibrillar cellulose hydrogels were carried out with a stress controlled rotational rheometer (ARG2, TA instruments, UK) equipped with four-bladed vane geometry. Samples were diluted with deionized water (200 g) to a concentration of 0.5 w % and mixed with Waring Blender (LB20E*, 0.5 l) 3×10 sec (20 000 rpm) with short break between the mixing. Rheometer measurement was carried out for the sample. The diameters of the cylindrical sample cup and the vane were 30 mm and 28 mm, respectively, and the length was 42 mm. The steady state viscosity of the hydrogels was measured using a gradually increasing shear stress of 0.001-1000 Pa. After loading the samples to the rheometer they weree allowed to rest for 5 min before the measurement was started, room temperature. The steady state viscosity was measured with a gradually increasing shear stress (proportional to applied torque) and the shear rate (proportional to angular velocity) was measured. The reported viscosity (=shear stress/shear rate) at a certain shear stress was recorded after reaching a constant shear rate or after a maximum time of 2 min. The measurement was stopped when a shear rate of 1000 s-1 was exceeded. The method was used for determining zero-shear viscosity. The viscosity properties of the hydrogels were also determined with the frequency sweep in dynamic oscillation mode of the rheometer (strain 1% and 10%, frequency 0.1-100, temperature 25° C.). The stress sweep was measured in a shear stress range of 0.001-100 Pa at the frequency 0.1 Hz, at 25° C.

Example 1

Pretreatment of Cellulose Pulp Followed by Fibrillation—Sample 1

2000 g of wet native cellulose pulp obtained from bleached birch pulp was filtered and the solid mass was diluted with 0.01M aqueous HCl and to obtain suspension having dry matter content of approx. 1% by weight. The suspension was allowed to stand for approx. 15 min with occasional agitation. The suspension was then filtered, washed twice with deionized water and filtered. Then the solid mass was suspended in a 0.005 M aqueous $NaHCO_3$ solution to obtain suspension having dry matter content of approx. 1% by weight, the pH of the obtained suspension was adjusted between 8 and 9 with 1 M aqueous NaOH solution and the obtained suspension was allowed to stand for 15 min with occasional agitation. The suspension was filtered and the solid mass was washed with deionized water until the conductivity of the filtrate was less than 20 µS/cm. The final conductivity was 8 µS/cm and pH 8.4.

Washed pulp was pre-refined with PFI mill. Standard refining was done until target SR value >75 was reached. The SR value after the pre-refining was 80.2.

The pre-refined sample was diluted to 1.7 w % consistency and followed by fibrillation in Microfluidics Fluidizer (M-7115-30), once through APM+200 µm chambers and through APM+100 µm (1500 bar) chambers until the turbidity was below the target level <200 NTU. The final turbidity for the product, Sample 1, was 136 NTU.

DP of the starting material was 2780 and DP of the final product Sample 1 was 1580 Table 1 illustrates the fiber size measured by Metso F5.

| Fiber size fraction | | Sample 1 |
|---|---|---|
| FS5 Fiber fractions 0-0.2 mm | % | 95.93 |
| FS5 Fiber fractions 0.2-0.6 mm | % | 3.19 |
| FS5 Fiber fractions 0.6-1.2 mm | % | 0.49 |
| FS5 Fiber fractions 1.2-2.0 mm | % | 0.39 |
| FS5 Fiber fractions 2.0-3.2 mm | % | 0.00 |
| FS5 Fiber fractions 3.2-7.6 mm | % | 0.00 |

The crystallinity index of the starting material of was 77 and the crystallinity index of the final product Sample 1 was 71.

Example 2

Pretreatment of Cellulose Pulp Followed by Fibrillation—Sample 2

2000 g of wet native cellulose pulp obtained from bleached birch pulp was filtered and the solid mass was diluted with 0.01M aqueous HCl and to obtain suspension having dry matter content of approx. 1% by weight. The suspension was allowed to stand for approx. 15 min with occasional agitation. The suspension was then filtered, washed twice with deionized water and filtered. Then the solid mass was suspended in a 0.005 M aqueous $NaHCO_3$ solution to obtain suspension having dry matter content of approx. 1% by weight, the pH of the obtained suspension was adjusted between 8 and 9 with 1 M aqueous NaOH solution and the obtained suspension was allowed to stand for 15 min with occasional agitation. The suspension was filtered and the solid mass was washed with deionized water until the conductivity of the filtrate was less than 20 µS/cm.

Washed pulp was pre-prefined with PFI mill. Standard refining was done until target SR value >75 was reached. The SR value after the pre-refining was 86.0.

The pre-refined sample was diluted to 1.5 w % consistency and followed by fibrillation in Microfluidics Fluidizer (M-110Y), once through APM+200 µm chambers and through APM+100 µm (1500 bar) chambers until the turbidity was below the target level <200 NTU. The final turbidity for the product, Sample 2, was 127 NTU.

DP of the starting material was 2833 and DP of the final product Sample 2 was 1640.

The crystallinity index of the starting material of was 75 and the crystallinity index of the final product Sample 2 was 66.

Example 3

FE-SEM Size Measurement

Figure 2:
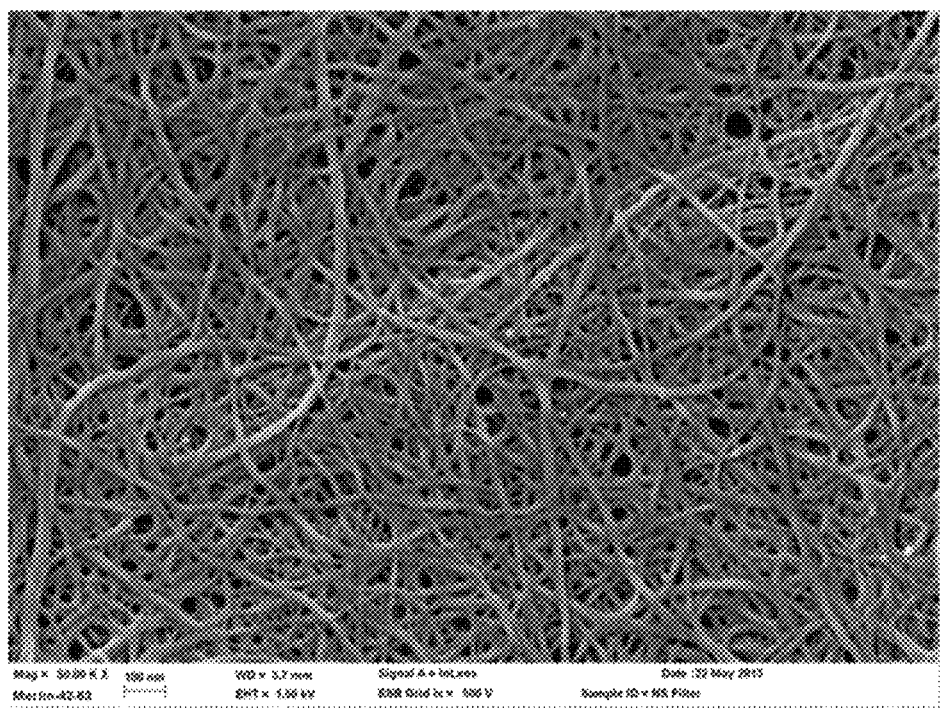
FIG. 2 presents FE-SEM image of nanofibrillar cellulose hydrogel, magnification 50 000×, scale bar 100 nm.
Figure 3:
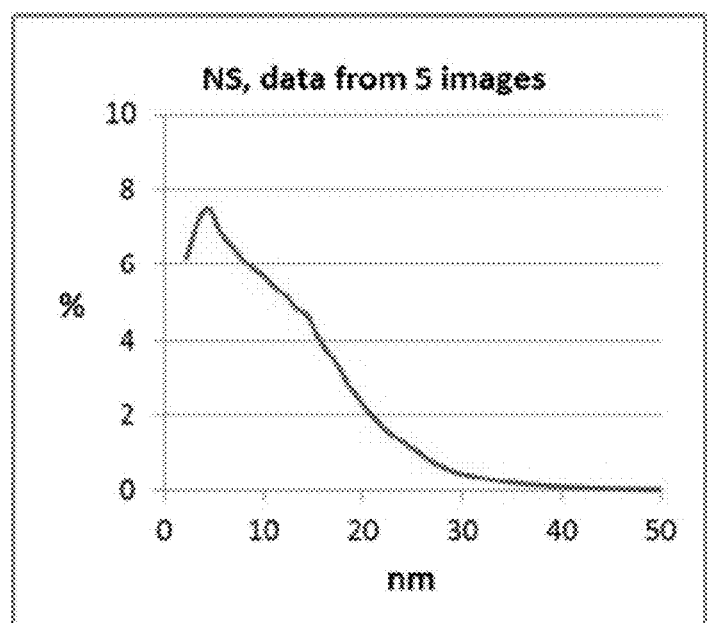
FIG. 3 presents fibril width distribution measured with an automatic image analysis routine, from the FE-SEM 5 images taken with magnification 50 000×.

Width and length of the nanofibrillar cellulose fibrils of Sample 1 were measured from the FE-SEM pictures. Fibril width distribution was measured with an automatic image analysis routine from 5 images, magnification 50 000×. FIG. 2 as an example. Analysis data is illustrated in FIG. 3. The number average diameter is between 2 and 15 nm. The fibril length is measured/estimated by following the fibrils with microscopy form picture to picture, magnification 5 000× and magnification 10 000×. The number average length is between 2 and 20 µm. FIG. 4 and FIG. 5 are presented as examples. Based on the results the average aspect ratio l/w was calculated. The average aspect ratio was greater than 500.

Example 4

Gel Properties by Rheological Measurements

To verify the preferred gel properties, rheological measurements of the samples in the form of nanofibrillar cellulose hydrogels were carried out with a stress controlled rotational rheometer. FIG. 6 presents the flow profiles of Sample 1 and Sample 2 dispersions as function of applied shear stress. Both samples are measured as such and after the dilution to 0.5 wt % consistency.

Figure 7:
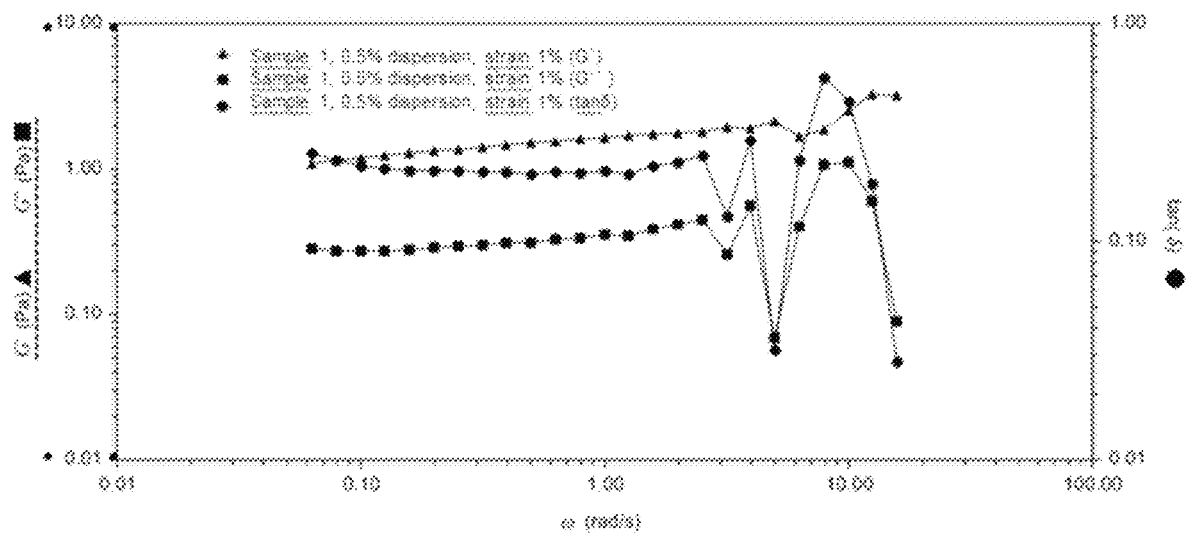
FIG. 7 illustrates the visco-elastic properties of 0.5% NFC dispersion of Sample 1 by frequency-sweep measurement (constant strain 10%). Stress dependence of G' (the storage modulus) and G" (the loss modulus) and a loss tangent are presented.
Figure 8:
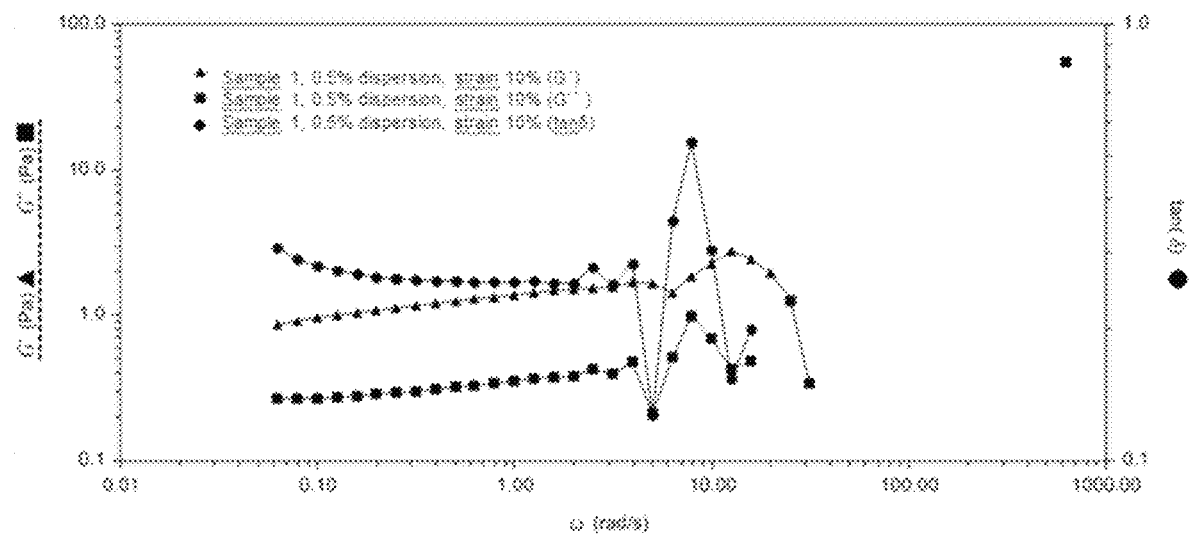
FIG. 8 illustrates the visco-elastic properties of 0.5% NFC dispersion of Sample 1 by frequency-sweep measurement (constant strain 10%). Stress dependence of G' (the storage modulus) and G" (the loss modulus) and a loss tangent are presented.

The Frequency sweep measurement of Sample 1 was performed in 0.5 wt % to verify that the gel strength is sufficient, which is, a loss tangent (tan δ) is less than 0.3. The frequency sweep is illustrated in FIG. 7. The loss tangent (tan δ) was 0.20 and the storage modulus (G') was 2 Pa at a frequency of 1 rad/s, 1% strain. The frequency sweep in 0.5 wt % using constant strain 10% was also measured, FIG. 8.

Figure 9:
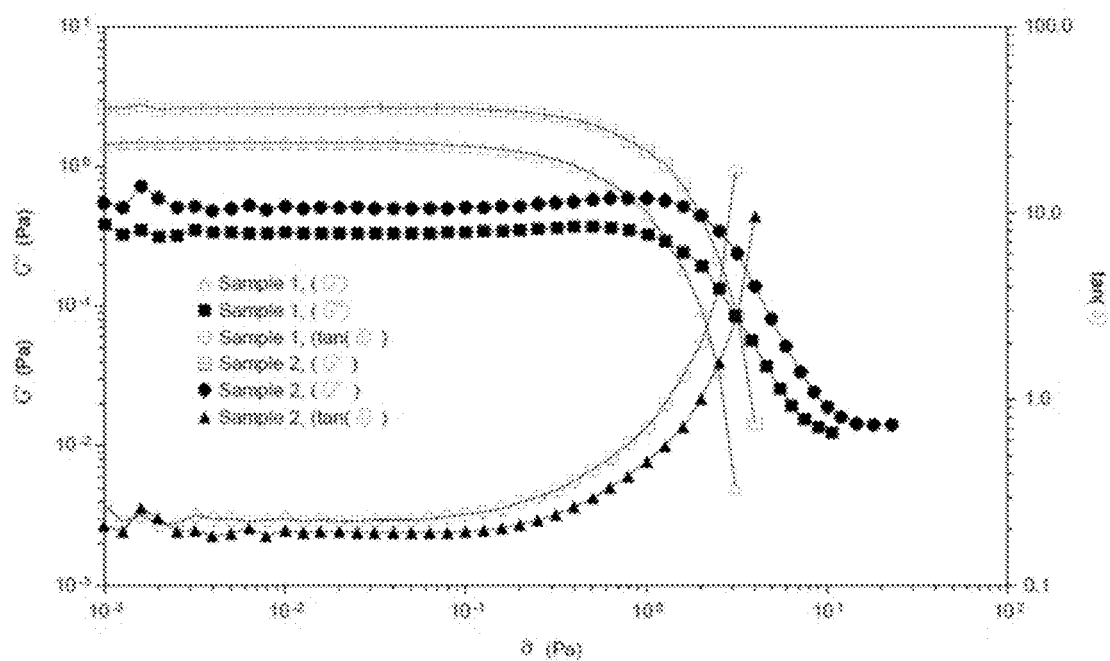
FIG. 9 illustrates the visco-elastic properties of 0.5% NFC dispersions of Sample 1 and Sample 2 by stress-sweep measurement. Stress dependence of G' (the storage modulus) and G" (the loss modulus) and a loss tangent are presented.

FIG. 9 presents the Stress Sweep of Sample 1 and Sample 2 dispersions in 0.5 wt % consistency. Sample 1 loss tangent (tan δ) was 0.21 and the storage modulus (G') was 1.5 Pa at a shear stress 0.1 Pa, frequency 0.1 Hz. Sample 2 loss tangent (tan δ) was 0.18 and the storage modulus (G") was 2.7 Pa at a shear stress 0.1 Pa, frequency 0.1 Hz.

REFERENCES

Bhattacharya M. et al. Nanofibrillar cellulose hydrogel promotes three-dimensional liver cell culture. J. Control. Release 164 (2012) 291-298.

Pääkkö M. et al. Enzymatic hydrolysis combined with mechanical shearing and hig-pressure homogenization for nanoscale cellulose fibrils and strong gels. Biomacromolecules 8 (2007) 1934-1941.

The invention claimed is:

1. A nanofibrillar cellulose, wherein said nanofibrillar cellulose is a high pressure mechanically disintegrated nanofibrillar cellulose in the form of a hydrogel or membrane, has an average degree of polymerization greater than 1000, and a storage modulus between 0.3 and 20 Pa, when dispersed to a concentration of 0.5 w % in water, and wherein said nanofibrillar cellulose is of plant origin, delaminated cellulose pulp, wherein the nanofibrillar cellulose has a number average diameter between 2 and 15 nm.

2. The nanofibrillar cellulose according to claim 1, wherein said nanofibrillar cellulose has an average degree of polymerization greater than 1150.

3. The nanofibrillar cellulose according to claim 1, wherein said nanofibrillar cellulose is of wood origin.

4. The nanofibrillar cellulose according to claim 1, wherein said nanofibrillar cellulose is of native cellulose.

5. The nanofibrillar cellulose according to claim 1, wherein said nanofibrillar cellulose has a turbidity of 200 NTU or less in water at concentration of 0.1 w %.

6. A nanofibrillar cellulose, wherein said nanofibrillar cellulose is a high pressure mechanically disintegrated nanofibrillar cellulose in the form of a hydrogel or membrane, has an average degree of polymerization greater than 1000, and a storage modulus between 0.3 and 20 Pa, when dispersed to a concentration of 0.5 w % in water, and wherein said nanofibrillar cellulose is of plant origin, delaminated cellulose pulp, wherein the crystallinity of the nanofibrillar cellulose is from 60% to 80%.

7. A nanofibrillar cellulose, wherein said nanofibrillar cellulose is a high pressure mechanically disintegrated nanofibrillar cellulose in the form of a hydrogel or membrane, has an average degree of polymerization greater than 1000, and a storage modulus between 0.3 and 20 Pa, when dispersed to a concentration of 0.5 w % in water, and wherein said nanofibrillar cellulose is of plant origin, delaminated cellulose pulp, wherein the nanofibrillar cellulose has a hemicellulose content greater than 10 w %.

8. The nanofibrillar cellulose according to claim 1, wherein the nanofibrillar cellulose has a number average length between 2 and 20 μm.

9. The nanofibrillar cellulose according to claim 1, wherein the nanofibrillar cellulose has an average aspect ratio greater than 500.

10. The nanofibrillar cellulose according to claim 1, wherein the nanofibrillar cellulose has a zero shear viscosity in the range of 100-8 000 Pa·s when dispersed to a concentration of 0.5 w % in water.

11. The nanofibrillar cellulose according to claim 1, wherein the nanofibrillar cellulose has a loss tangent less than 0.3 when dispersed to a concentration of 0.5 w % in water.

12. A nanofibrillar cellulose, wherein said nanofibrillar cellulose is a high pressure mechanically disintegrated nanofibrillar cellulose in the form of a hydrogel or membrane, has an average degree of polymerization greater than 1000, and a storage modulus between 0.3 and 20 Pa, when dispersed to a concentration of 0.5 w % in water, and wherein said nanofibrillar cellulose is of plant origin, delaminated cellulose pulp, wherein more than 90% by weight of the nanofibrillar cellulose is in the fiber fraction of less than 0.2 mm.

13. A membrane comprising the nanofibrillar cellulose as defined in claim 1.

14. The nanofibrillar cellulose according to claim 1 for use as a pharmaceutical.

15. The nanofibrillar cellulose according to claim 1 for use in or as a matrix for drug delivery, cell delivery, tissue engineering, wound treatment, or implants, or as a wound healing agent, an anti-inflammatory agent, or a hemostatic agent.

16. A pharmaceutical, cosmetic, food, agrochemical, paint, coating, paper, board, pulp, filter, composite product, adhesive, display, personal care composition, tooth paste, or cell or tissue culture matrix, or cell or tissue delivery matrix comprising the nanofibrillar cellulose as defined in claim 1.

17. The nanofibrillar cellulose according to claim 1, wherein the cellulose pulp includes cations, said cations having replaced cations present in native cellulose pulp, the cellulose pulp having a freeness of at least 60° SR (Schopper-Riegler).

* * * * *